United States Patent
Mizutani et al.

(10) Patent No.: US 6,602,236 B1
(45) Date of Patent: *Aug. 5, 2003

(54) SANITARY NAPKIN

(75) Inventors: Satoshi Mizutani, Kagawa-ken (JP); Wataru Yoshimasa, Kagawa-ken (JP)

(73) Assignee: Uni-Charm Corp., Ehime-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/522,143

(22) Filed: Mar. 9, 2000

(30) Foreign Application Priority Data

Mar. 11, 1999 (JP) .............................. 11-065470

(51) Int. Cl.[7] .................................. A61F 13/15
(52) U.S. Cl. .................. 604/385.04; 604/387
(58) Field of Search .................... 604/385.03, 385.04, 604/385.05, 386, 387, 389, 390

(56) References Cited

U.S. PATENT DOCUMENTS

| | | | | |
|---|---|---|---|---|
| 5,387,210 A | * | 2/1995 | Murakami | 604/387 |
| 5,490,847 A | * | 2/1996 | Correa et al. | 604/387 |
| 5,542,941 A | * | 8/1996 | Morita | 604/387 |
| 5,591,147 A | | 1/1997 | Couture-Dorschner et al. | |
| 5,649,917 A | * | 7/1997 | Roberts et al. | 604/387 |
| 5,704,928 A | * | 1/1998 | Morita et al. | 60/387 |
| 5,752,947 A | * | 5/1998 | Awolin | 604/387 |
| 5,820,618 A | * | 10/1998 | Roberts et al. | 604/387 |
| 5,921,975 A | * | 7/1999 | Suzuki et al. | 604/387 |

FOREIGN PATENT DOCUMENTS

| | | |
|---|---|---|
| EP | 0 595 047 A | 5/1994 |
| EP | 0 852 133 A | 7/1998 |
| EP | 0 998 893 A | 5/2000 |
| GB | 2 296 445 A | 7/1996 |
| JP | 2-7956 | 1/1990 |
| WO | WO 95/08311 A | 3/1995 |
| WO | WO 96/23471 A | 8/1996 |

OTHER PUBLICATIONS

Copy of European Search Report mailed Feb. 13, 2001.

* cited by examiner

Primary Examiner—Dennis Ruhl
(74) Attorney, Agent, or Firm—Butzel Long

(57) ABSTRACT

A sanitary napkin 1 includes respective pairs of upper and lower layer flaps 11, 12 placed upon each other, each of the upper layer flaps 11 is elastically stretchable longitudinally of the napkin 1 and each of the lower layer flaps 12 is provided with a wing 13, and thereby prevent the menstrual discharge from leaking sideways.

8 Claims, 5 Drawing Sheets

SANITARY NAPKIN

BACKGROUND OF THE INVENTION

This invention relates to a sanitary napkin for absorption and containment of the menstrual discharge.

Japanese Patent Application Disclosure No. 1990-7956 describes a sanitary napkin having a pair of wings on its sides. According to this Application, the napkin is formed along its transversely opposite side edges with flaps adapted to be stretchable longitudinally of the napkin. Portions of these flaps extending outward from an undergarment worn by the wearer beyond peripheries of leg-openings are stretchable to follow the curvature of the peripheries as these portions when folded onto the outer surface of the crotch region of the undergarment. The portions of the flaps folded in this manner can be fastened to the outer surface of the undergarment by means of adhesive agent applied on the flaps.

The known napkin as has been mentioned above enables the flaps to cover the peripheries of leg-openings of the undergarment and thereby to prevent the peripheries from being stained with the menstrual discharge. However, it is still difficult for the known napkin to prevent the menstrual discharge leaking sideways from flowing down along the wearer's thighs.

SUMMARY OF THE INVENTION

It is an object of this invention to provide a sanitary napkin that is adapted to be fastened to the outer surface of the undergarment worn by the wearer so that menstrual discharge leaking sideways from the undergarment can be reliably prevented from flowing down along the wearer's thighs.

According to this invention, there is provided a sanitary napkin having a pair of transversely opposite side edges extending longitudinally of the napkin and a pair of longitudinally opposite ends extending transversely of the napkin, the napkin comprising: a liquid-pervious topsheet, a liquid-impervious backsheet, and a liquid-absorbent core disposed therebetween; the transversely opposite side edges comprising upper and lower layer flaps separably placed upon each other, each of the upper layer flaps having a length corresponding to 1/2~1/1 of a full length of the napkin, the maximum width of 10~30 mm and an elastic stretchability of 120~300% longitudinally of the napkin, and each of the lower layer flaps laterally extending outward beyond an outer side edge of the upper layer flap and including a wing coated on a lower surface thereof with an adhesive agent.

This invention includes embodiments that: each of the upper layer flaps is formed by a sheet being elastically stretchable at least longitudinally thereof; each of the upper layer flaps comprises a sheet being non-stretchable longitudinally thereof and an elastic member secured thereto under tension longitudinally thereof to form the sheet with a plurality of gathers defined by crests and troughs alternately arranged longitudinally thereof; each of the upper layer flaps comprises the non-stretchable sheet formed with a plurality of zones crowded with the gathers so that these zones are intermittently arranged longitudinally of the non-stretchable sheet; and the lower layer flaps are elastically stretchable longitudinally thereof.

DETAILED DESCRIPTION OF THE PREFERRED EMBODIMENTS

Details of a sanitary napkin according to this invention will be more fully understood from the description given hereunder with reference to the accompanying drawings.

Figure 1:
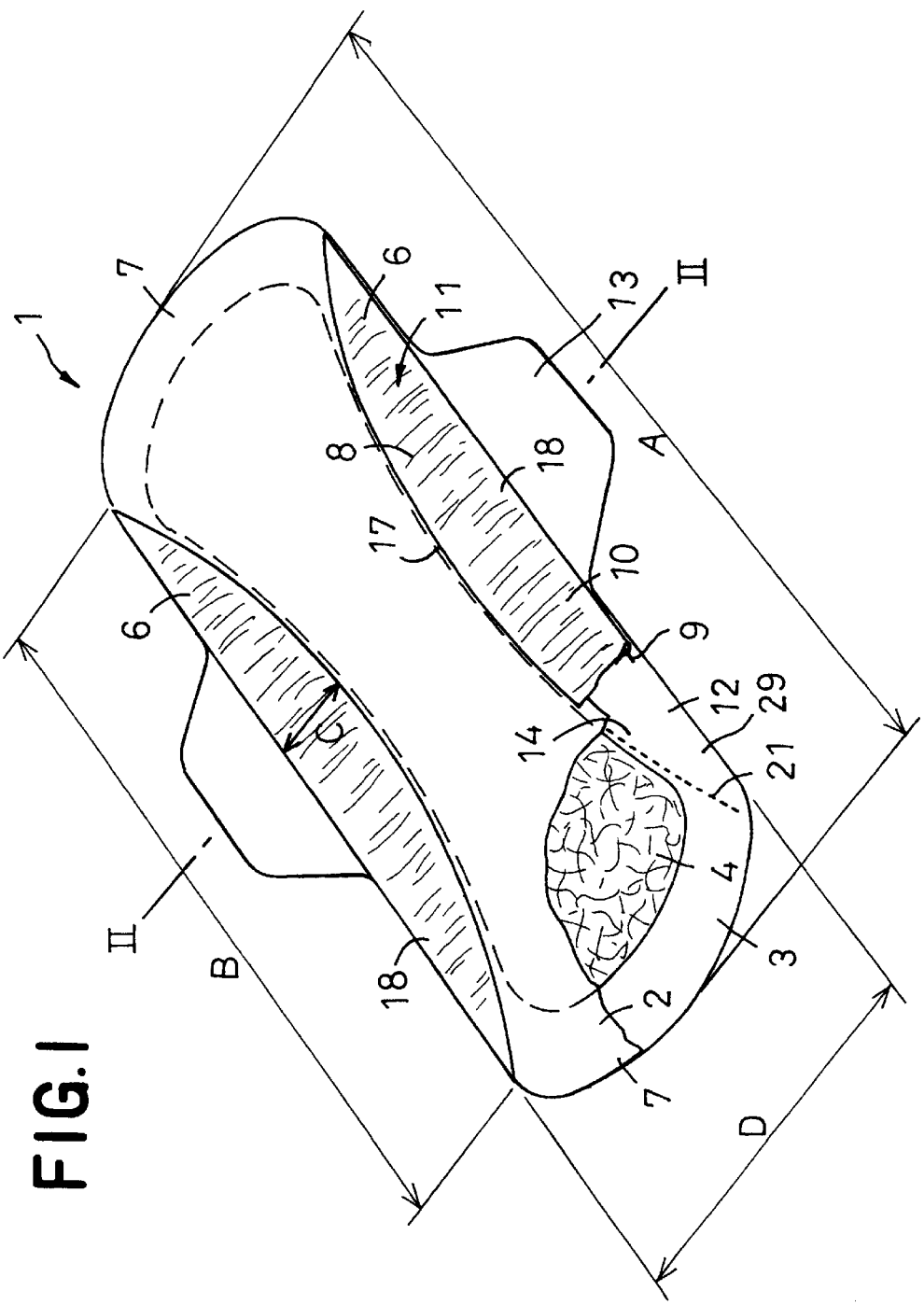
FIG. 1 is a perspective view of a partially cutaway sanitary napkin according to this invention.

FIG. 1 is a perspective view of a partially cutaway sanitary napkin 1. The napkin 1 has a pair of transversely opposite side edges 6 extending longitudinally of the napkin 1 and a pair of longitudinally opposite ends 7 extending transversely of the napkin 1, and comprises a liquid-pervious topsheet 2, a liquid-impervious backsheet 3 and a liquid-absorbent core 4 disposed between these two sheets 2, 3. The topsheet 2 and the backsheet 3 extend outward beyond a peripheral edge of the absorbent core 4 and are joined to each other along these extensions. The side edges 6 have upper layer flaps 11 each comprising a sheet 10 having a plurality of gathers 8 formed by crests and troughs transversely extending and alternately arranged longitudinally of the napkin 1 and an elastic member 9 extending longitudinally of the napkin 1, and lower layer flaps 12 each underlying the upper layer flap 11 and provided with a wing 13. The absorbent core 4 is generally hour glass, shaped.

Figure 2:
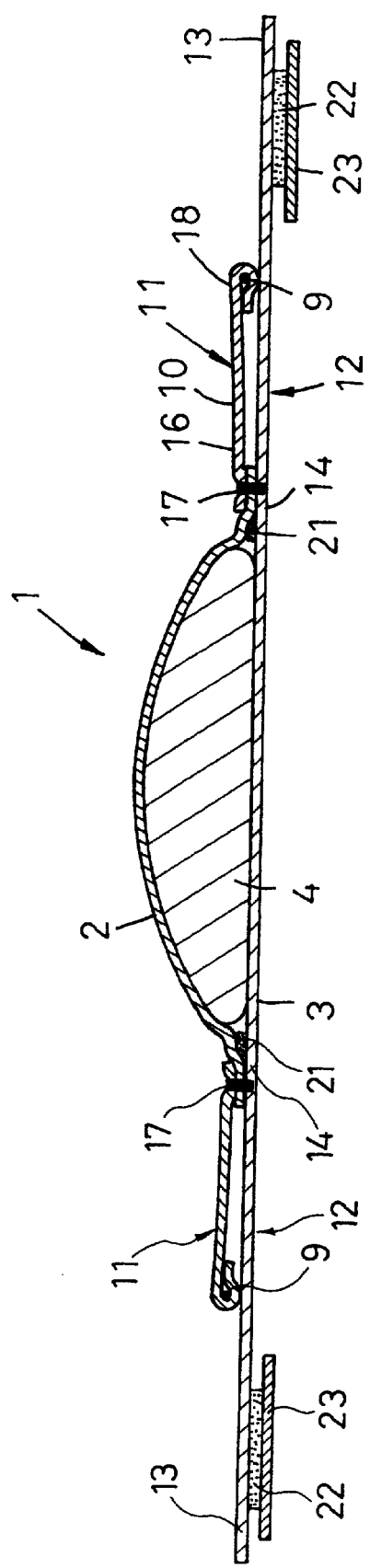
FIG. 2 is a sectional view taken along a line II—II in FIG. 1.

FIG. 2 is a sectional view taken along a line II—II in FIG. 1. The sheet 10 making a part of the upper layer flap 11 may be a non-stretchable or stretchable sheet and the inner edge 16 of this upper layer flap 11 may be joined to the side edge of the topsheet 2 and/or to a portion of the backsheet 3 extending laterally beyond the side edge of the topsheet 2 along a joining line 17. Along the outer side edge 18 of the upper layer flap 11, the sheet 10 is folded downward to wrap the elastic member 9 which is, in turn, secured under tension to the inner side of the sheet 10 so that the gathers 8 are formed under contraction of this elastic member 9. A stretch stress of the elastic member 9 as this elastic member 9 is secured to the sheet 10 is preferably in a range of 10~150 g. As will be apparent from FIGS. 1 and 2, the joining line 17 for the inner side edge 16 longitudinally extending along the side edge of the absorbent core 4 describes a curve convex inwardly of the napkin 1 and its longitudinally opposite ends cross the outer side edge 18 of the upper layer flap 11. A longitudinal dimension B of the upper layer flap 11 is in a range of 1/2~1/1 of a full length A of the napkin 1 and preferably can be stretched to 200 mm or larger. The maximum transverse dimension C of the upper layer flap 11 is preferably in a range of 10~30 mm. A dimension D between the outer side edges 18 of the pair of upper layer flaps 11 is preferably in a range of 60~120 mm and more preferably in a range of 80~100 mm.

Each of the lower layer flaps 12 has its proximal side edge 14 formed by the portions of the topsheet 2 and the backsheet 3 extending laterally beyond the side edge of the absorbent core 4. These two sheets 2, 3 are placed upon and joined to each other by means of hot melt adhesive agent in the vicinity of the side edge of the absorbent core 4. The backsheet 3 further extends laterally beyond the side edge of the topsheet 2 to the outer side edge 18 of the upper layer flap 11 and partially further extends laterally to the wing 13. The lower surface of the wing 13 is coated with an adhesive agent 22 which is, in turn, protected by a release sheet 23.

Figure 3:
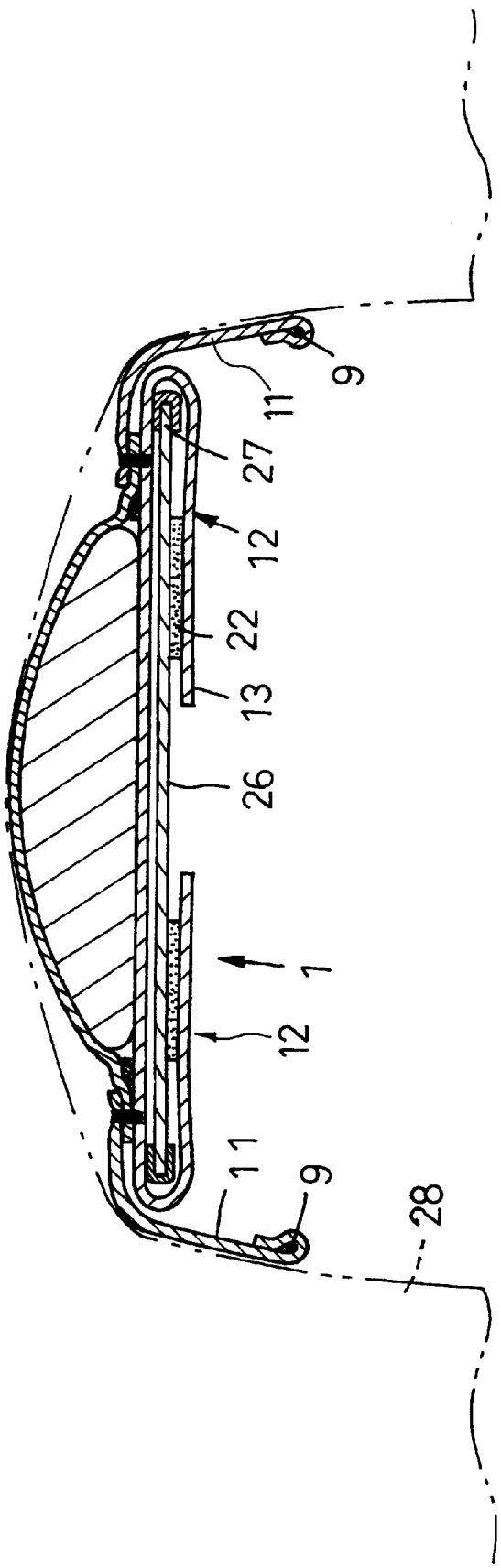
FIG. 3 is a sectional view of the napkin in its flat condition as put on the wearer's body.

FIG. 3 is a sectional view of the napkin 1 of FIG. 1 as put on the wearer's body. As shown, the napkin 1 is placed on the inner surface of a crotch region of an undergarment and the lower layer flaps 12 are folded onto the outer surface of the crotch region with the wings 13 fastened to the outer surface by means of the adhesive agent 22. The lower layer flaps 12 folded in this manner cover the peripheries 27 of leg-openings of the undergarment 26 and prevent the peripheries 27 from being soiled with the menstrual discharge.

The upper layer flaps 11 are folded downward along the peripheries 27 of the leg-openings of the undergarment 26 and closely pressed against the wearer' thighs 28. This is because the gathers 8 as well as the elastic members 9 are forcibly stretched longitudinally of the napkin 1 as the upper layer flaps 11 are folded downward and therefore the gathers 8 as well as the elastic members 9 are biased to restore their initial positions that is, the napkin 1 is in its flat condition as shown in FIG. 2. Therefore, the upper layer flaps 11 prevent the menstrual discharge from leaking at side edges of the napkin 1 and flowing down along the inner sides of the wearer's thighs 28.

Figure 4:
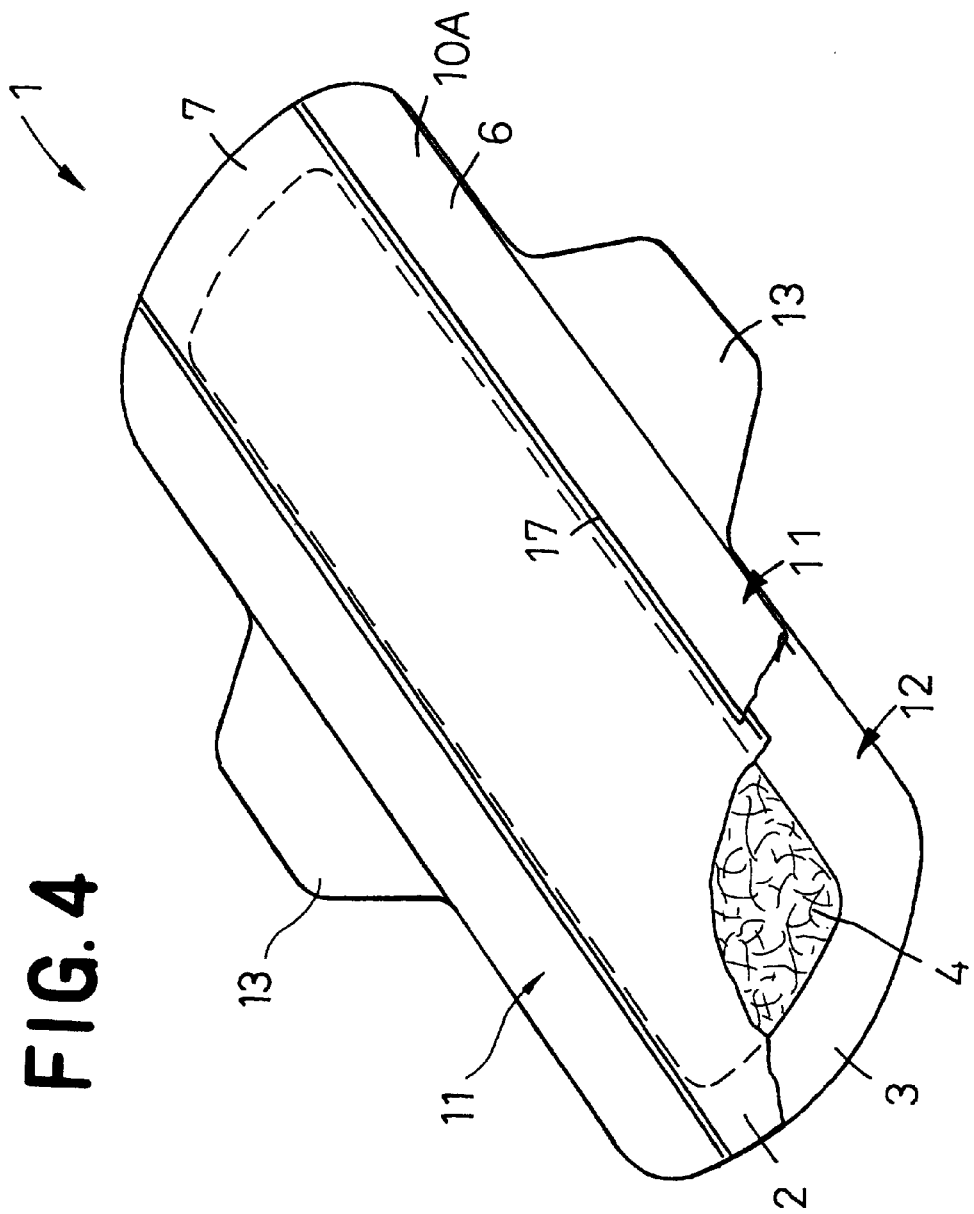
FIG. 4 is a view similar to FIG. 1 of one embodiment.

FIG. 4 is a view similar to FIG. 1 of one embodiment of this invention. With this napkin, the absorbent core 4 has a rectangular shape and, along the transversely opposite side edges of the absorbent core 4, substantially rectangular upper layer flaps 11 and the lower layer flaps 12 provided with the wings 13 are formed. The upper layer flaps 11 are similar to them of FIG. 1 in that each of them extends substantially over the full length of the napkin 1 and has a width of 10~30 mm but different from those of FIG. 1 in that an elastic sheet 10A being stretchable by 120~300% at least longitudinally thereof is used as stock material for the upper layer flaps 11. The lower layer flaps 12 are similar to those of FIG. 1. The napkin 1 according to this embodiment also takes the same posture as the napkin 1 of FIG. 1 when the napkin 1 is put on the wearer. The elastic sheet 10A may be a stretchable sheet such as a natural rubber sheet or synthetic rubber sheet.

Figure 5:
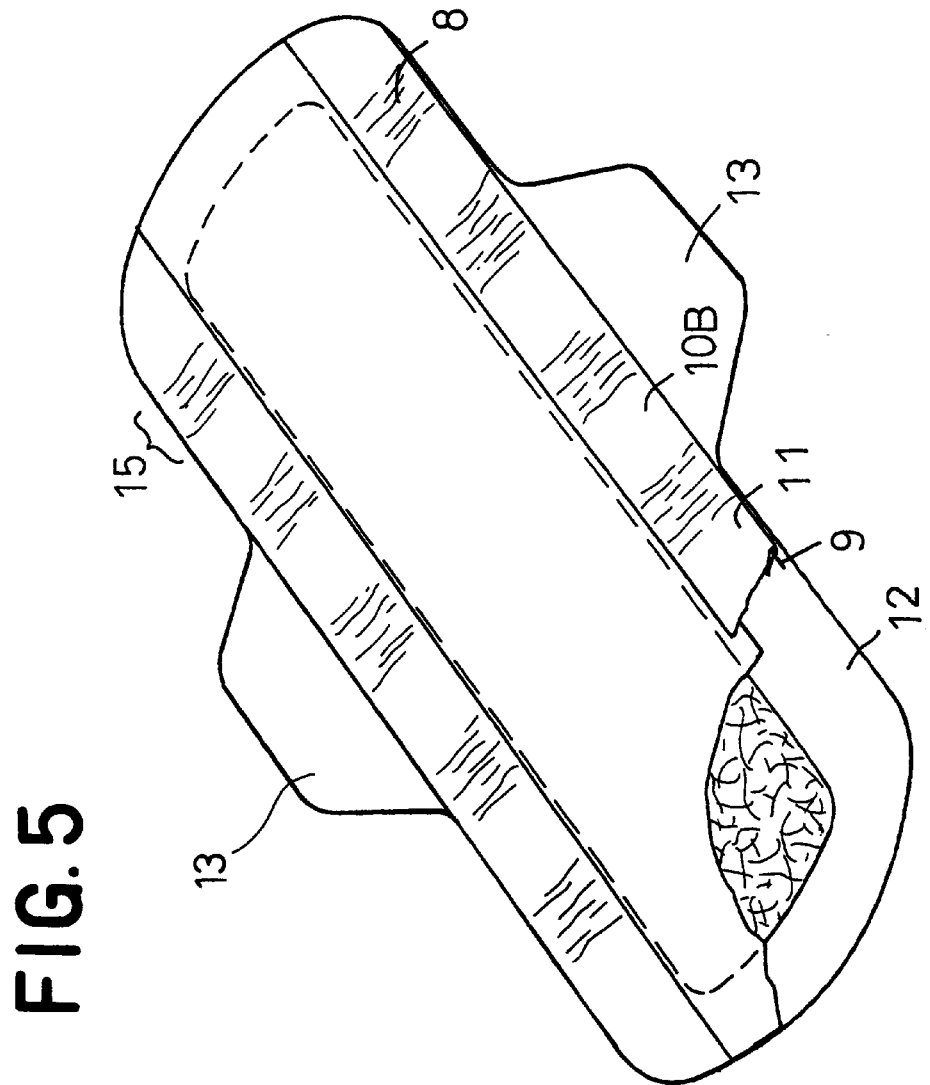
FIG. 5 is a view similar to FIG. 1 of another embodiment.

FIG. 5 is also a view similar to FIG. 1 of another embodiment of this invention. According to this embodiment, each of the upper layer sheets 11 is formed by a sheet 10B which is non-stretchable longitudinally thereof and zones 15 crowded with gathers 8 defined by crests and troughs are alternately and intermittently arranged. The upper layer flaps 11 provided along their outer side edges with the elastic members 9 and the gathers 8 as well as the elastic members 9 are forcibly stretched longitudinally thereof as the napkin 1 is put on the wearer's body as shown in FIG. 3. In this manner, the upper layer flaps 11 are closely pressed against the wearer's thighs 28.

For exploitation of this invention, a nonwoven fabric or porous plastic film may be used as stock material for the topsheet 2. As stock material for the backsheet 3, a plastic film may be used. The absorbent core 4 may be formed by a fluff pulp or a mixture of fluff pulp and superabsorptive polymer particles. Stock material for the upper layer flaps 11 may be formed by a stretchable or non-stretchable and, in addition, preferably breathable, more preferably, breathable and sweat-absorbent nonwoven fabric or plastic film. While the lower layer flaps 12 are formed by portions of the backsheet 3 widely extending laterally in the illustrated embodiments, it is also possible for the lower layer flaps 12 to be formed by a nonwoven fabric or plastic film provided separately of the topsheet 2 and the backsheet 3 and joined to the topsheet 2 and/or the backsheet 3. In order to facilitate the lower layer flaps 12 to be folded along the leg-openings of the undergarment, not only the proximal side edges 14 may be curved as shown in FIG. 1 but also the outer side edges 29 (See FIG. 1) may be curved inwardly of the napkin 1. A dimension by which each of the lower layer flaps 12 extends laterally may be selected independently of such dimension in the upper layer flaps 12. However, it is obvious that the wings 13 should have sufficient dimensions to reach the crotch region of the undergarment regardless the dimension of the lower layer flaps 12. Furthermore, the lower layer flaps 12 may have an elastic stretchability also longitudinally thereof. Joining of the topsheet 2 and the backsheet 3 and the upper and lower layer flaps 11, 12 may be performed using a suitable adhesive agent such as a hot melt adhesive agent or sealing technique such as heat-sealing technique.

The sanitary napkin according to this invention has the upper layer flaps and the lower layer flaps so that the upper layer flaps may be closely pressed against the wearer's thighs and the lower layer flaps may be folded onto the outer surface of the crotch region of the undergarment with the wings being fastened to the outer surface. In this manner, the convenience for use offered by a so-called winged napkin is advantageously combined with the effect to prevent the menstrual discharge from flowing down along the wearer's thighs.

What is claimed is:

1. A sanitary napkin having a pair of transversely opposite edges extending longitudinally of said napkin and a pair of longitudinally opposite ends extending transversely of said napkin, said napkin comprising:

a liquid-pervious topsheet;

a liquid-impervious backsheet;

a liquid-absorbent core disposed between said topsheet and said backsheet; and upper and lower layer flaps extending longitudinally along and outward relative to each of said transversely opposite side edges, each of said upper layer flaps being formed from a sheet that is separate from said topsheet and said backsheet, each of said upper layer flaps being elastically stretchable in a longitudinal direction and having a plurality of gathers formed therein which plurality of gathers are provided along a length of each of said upper layer flaps, each of said upper layer flaps includes an inner side edge and an outer side edge, said inner side edge of each of said upper layer flaps being defined along lower transversely opposite side edges of said liquid-absorbent core, said plurality of gathers extending from said inner side edge to the outer side edge of each said upper layer flaps, each of said upper layer flaps being joined to at least one of portions of said topsheet and said backsheet adjacent said side edge of said napkin, each of said lower layer flaps including a wing that extends laterally outward beyond an outer side edge of said upper layer flap and each said wing includes a lower surface coated with an adhesive agent, each of said upper layer flaps comprising an elastic member secured under tension longitudinally thereof whereby the tension provided by the elastic member causes said plurality of gathers to form, each of said upper layer flaps is formed from a sheet that is elastically stretchable longitudinally thereof.

2. The napkin according to claim 1, wherein said core is generally hour-glass shaped.

3. The napkin according to claim 2, wherein the inner side edge of each of said upper layer flaps comprises a convex, curved inner side edge extending longitudinally, each of said lower layer flaps is joined to said inner side edge of one of said upper layer flaps, said lower layer flaps are defined by portions of said backsheet laterally extending outward from the side edges of said napkin.

4. The napkin according to claim 1, wherein the wings comprise portions of the liquid-impervious backsheet which extend beyond the liquid-absorbent core.

5. The napkin according to claim 1, wherein the each of the upper layer flaps includes a single elastic member that is secured under tension longitudinally thereof.

6. A sanitary napkin having a pair of transversely opposite edges extending longitudinally of said napkin and a pair of longitudinally opposite ends extending transversely of said napkin, said napkin comprising:

a body having transversely opposite side edges; and upper and lower layer flaps extending longitudinally along and outward relative to the transversely opposite side edges of the body, the body comprising:
a liquid-pervious topsheet;
a liquid-impervious backsheet; and
a liquid-absorbent core disposed between said topsheet and said backsheet, each of said upper layer flaps being formed from a sheet that is separate from said topsheet and said backsheet, each of said upper layer flaps including an inner side edge and an outer side edge and being elastically stretchable in a longitudinal direction and having a plurality of gathers formed therein which plurality of gathers are provided along a length of each of said upper layer flaps, said plurality of gathers extending from the inner side edge to the outer side edge of each of the upper layer flaps, each of said upper layer flaps being joined to at least one of portions of said topsheet and said backsheet adjacent said side edge of said napkin, each of said lower layer flaps including a wing that extends laterally outward beyond an outer side edge of said upper layer flap and each said wing includes a lower surface coated with an adhesive agent, each of said upper layer flaps comprises a sheet that is non-stretchable longitudinally thereof and an elastic member secured under tension longitudinally thereof whereby tension applied to said sheet by said elastic member forms said plurality of gathers in the sheet defined by crests and troughs alternatively arranged longitudinally thereof, each of said upper layer flaps being joined to and extending longitudinally along the opposite transverse edges of the body of the napkin, said plurality of gathers arranged in discrete zones, said zones being intermittently arranged longitudinally of said non-stretched sheet.

7. The napkin according to claim 6, wherein the inner side edge of each of said upper layer flaps comprises a convex, curved inner side edge extending longitudinally, each of said lower layer flaps is joined to said inner side edge of one of said upper layer flaps, said lower layer flaps are defined by portions of said backsheet laterally extending outward from the side edges of said napkin.

8. A sanitary napkin having a pair of transversely opposite edges extending longitudinally of said napkin and a pair of longitudinally opposite ends extending transversely of said napkin, said napkin comprising:

a liquid-pervious topsheet;
a liquid-impervious backsheet;
a liquid-absorbent core disposed between said topsheet and said backsheet; and upper and lower layer flaps extending longitudinally along and outward relative to each of said transversely opposite side edges, each of said upper layer flaps being formed from a sheet that is separate from said topsheet and said backsheet, each of said upper layer flaps being elastically stretchable in a longitudinal direction and having a plurality of gathers formed therein which plurality of gathers are provided along a length of each of said upper layer flaps, each of said upper layer flaps includes an inner side edge and an outer side edge, said inner side edge of each of said upper layer flaps being defined along lower transversely opposite side edges of said liquid-absorbent core, said plurality of gathers extending from said inner side edge to the outer side edge of each said upper layer flaps, each of said upper layer flaps being joined to at least one of portions of said topsheet and said backsheet adjacent said side edge of said napkin, each of said lower layer flaps including a wing that extends laterally outward beyond an outer side edge of said upper layer flap and each said wing includes a lower surface coated with an adhesive agent, each of said upper layer flaps comprising an elastic member secured under tension longitudinally thereof whereby the tension provided by the elastic member causes said plurality of gathers to form, wherein said lower layer flaps are elastically stretchable longitudinally thereof.

* * * * *